United States Patent
Clark

(10) Patent No.: US 6,644,323 B1
(45) Date of Patent: Nov. 11, 2003

(54) DENTAL IMPLANT FLOSS CONSTRUCTION

(76) Inventor: Kenneth E. Clark, 13961 Sand Hill Crane Dr., South Jacksonville, FL (US) 32224

(*) Notice: Subject to any disclaimer, the term of this patent is extended or adjusted under 35 U.S.C. 154(b) by 41 days.

(21) Appl. No.: 10/091,696

(22) Filed: Mar. 6, 2002

(51) Int. Cl.$^7$ ................................................ A61C 15/00
(52) U.S. Cl. ...................................... 132/321; 433/141
(58) Field of Search ............................... 132/321, 329; 433/141

(56) References Cited

U.S. PATENT DOCUMENTS

| | | | |
|---|---|---|---|
| 3,896,824 A | | 7/1975 | Thornton |
| 3,930,059 A | * | 12/1975 | Wells |
| 4,142,538 A | | 3/1979 | Thornton |
| 4,265,258 A | | 5/1981 | Eaton, II |
| 4,974,614 A | * | 12/1990 | Selker ........................ 132/321 |
| 5,063,948 A | | 11/1991 | Lloyd ......................... 132/321 |
| 5,392,794 A | * | 2/1995 | Striebel ...................... 132/324 |
| 5,560,377 A | * | 10/1996 | Donovan ..................... 132/321 |
| 5,566,691 A | * | 10/1996 | Dolan et al. ................. 132/321 |
| 5,682,911 A | * | 11/1997 | Harada ........................ 132/321 |
| 5,878,758 A | * | 3/1999 | Bacino et al. ............... 132/321 |
| 5,915,392 A | * | 6/1999 | Isaac .......................... 132/200 |
| 6,250,313 B1 | * | 6/2001 | Rees ........................... 132/321 |

* cited by examiner

*Primary Examiner*—Cary E. O'Connor
(74) *Attorney, Agent, or Firm*—Sturm & Fix LLP

(57) ABSTRACT

An improved dental floss construction (10) for removing plaque and food particles from the periphery of the metal support posts (101) for a dental implant (100) wherein the construction (10) includes a pair of deformable end units (11) wherein each end unit (11) has a very thin strand of wire (20) encapsulated in a very thin layer of plastic; wherein, each strand of wire (20) has an inboard end (21).

In addition, the construction (10) further includes an intermediate flossing unit (12) having a length of flossing material (30) such as plastic yarn whose opposite ends are supported by the inboard ends (24) of each strand of wire (20).

12 Claims, 1 Drawing Sheet

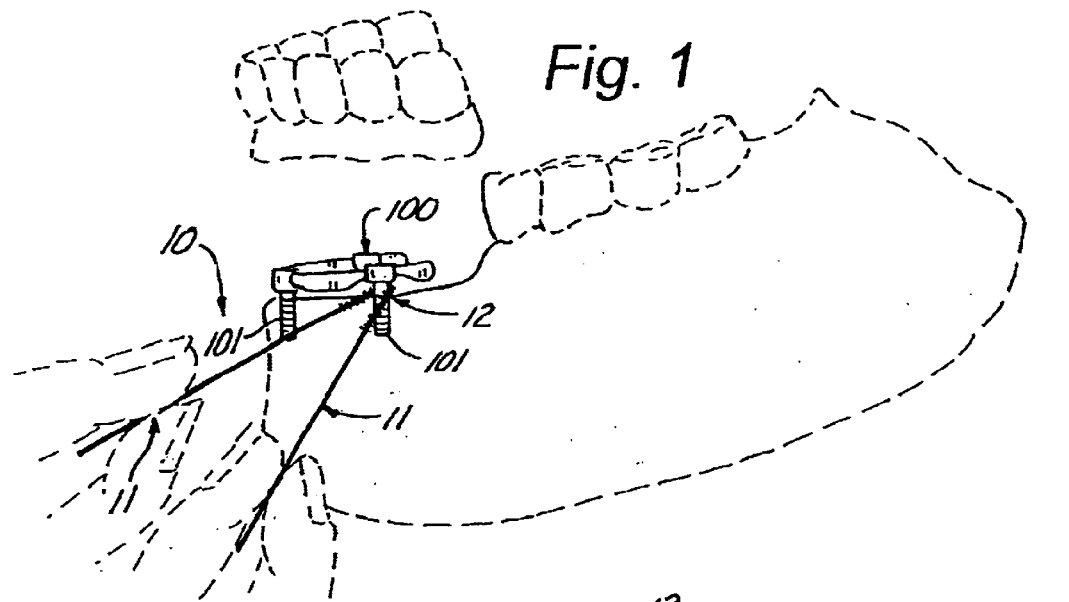
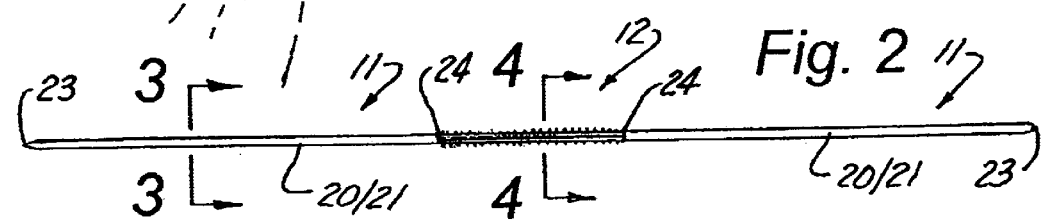
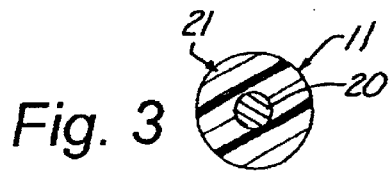 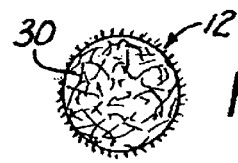
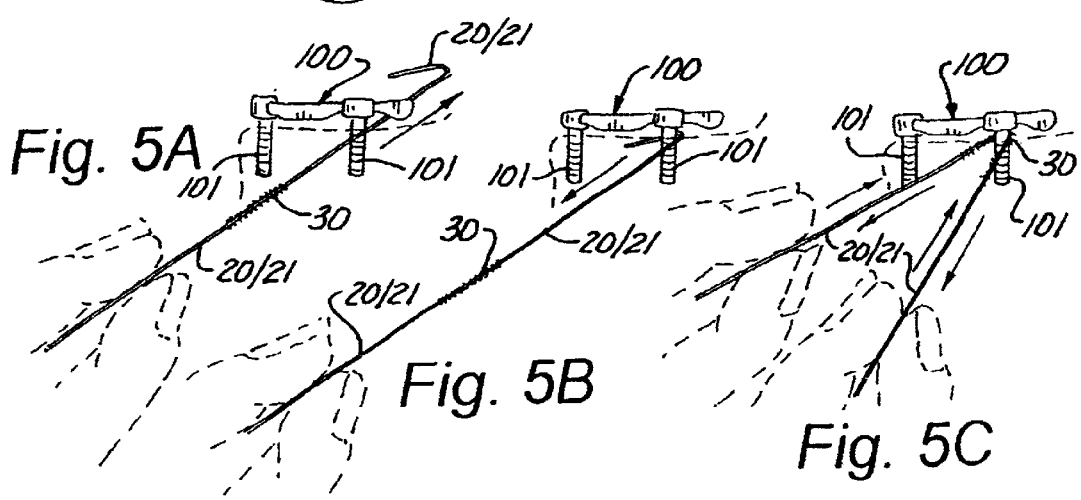

DENTAL IMPLANT FLOSS CONSTRUCTION

CROSS REFERENCE TO RELATED APPLICATIONS

This application was the subject matter of Disclosure Document Program Registration #477,293, filed on Jul. 24, 2000.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to the field of dental floss constructions in general and in particular to a dental floss construction specifically designed for use with the posts employed on dental implants.

2. Description of Related Art

As can be seen by reference to the following U.S. Pat. Nos. 3,896,824; 4,142,538; 4,265,258; and, 5,063,948, the prior art is replete with myriad and diverse dental floss constructions.

While all of the aforementioned prior art constructions are more than adequate for the basic purpose and function for which they have been specifically designed, they are uniformly deficient with respect to their failure to provide a simple, efficient, and practical dental floss construction that is specifically designed to clean the posts that support dental implants.

As most dental implant wearers are all too well aware, a crucial part of the their dental hygiene regimen involves removing trapped food particles and plaque that are deposited on and build up around the metal posts that support the dental implant.

Unfortunately, none of the aforementioned prior art constructions are particularly well suited to address this pressing problem which faces a growing number of dental implant wearers each day.

As a consequence of the foregoing situation, there has existed a longstanding need among people having dental implants for a new and improved dental floss construction that is specifically designed to address the problem of removing food particles and plaque from the periphery of dental implant support posts; and, the provision of such a construction is a stated objective of the present invention.

BRIEF SUMMARY OF THE INVENTION

Briefly stated, the dental floss construction that forms the basis of the present invention comprises a pair of deformable end units and an intermediate flossing unit operatively connected between the deformable end units.

As will be explained in greater detail further on in the specification, the deformable end units each include a very thin malleable strand of wire, encapsulated in a thin layer of flexible plastic, wherein, the outboard ends of the end units are tapered and the inboard ends of the end units are flared to form an attaching surface for the opposite ends of the intermediate flossing unit.

In addition, the intermediate flossing unit comprises a length of flexible flossing material such as plastic yarn having a relatively high co-efficient of friction external periphery that acts like a plastic scouring pad to remove food and plaque particles from the periphery of the steel posts that support the dental implants in the area between the wearer's gum line and the bottom of the implants.

The malleable wire allows either end of the floss construction to be temporarily deformed into a narrow V-shaped hook that passes beneath the implant and is then withdrawn to capture the implant support post with the free end projecting outwardly from the user's mouth where it can be grasped to position the length of flexible flossing material in a substantially surrounding relationship with the periphery of the metal support post so that the reciprocal movement of the end units causes the intermediate flossing unit to scrub clean the periphery of the support post in a well recognized fashion.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a perspective view of the dental floss construction operatively engaged with one of the metal support posts of a dental implant;

FIG. 2 is an isolated perspective view of the dental floss construction;

FIG. 3 is a cross-sectional view of one of the end units taken through line 3—3 of FIG. 2;

FIG. 4 is a cross-sectional view of the intermediate flossing unit taken through line 4—4 of FIG. 2;

FIGS. 5 through 5c illustrate the manipulation of the dental floss construction to clean the periphery of the dental implant support posts.

DETAILED DESCRIPTION OF THE INVENTION

As can be seen by reference to the drawings, and in particularly to FIG. 1, the dental floss construction that forms the basis of the present invention is designated generally by the reference number 10. The dental floss construction 10 comprises in general a pair of deformable end units 11 and an intermediate flossing unit 12. These units will now be described in seriatim fashion.

As can best be seen by reference to FIGS. 2 and 3, each of the deformable end units 11 comprises a very thin strand of deformable metal wire 20 encapsulated in a generally thin layer of flexible plastic 21 wherein the composite structure 20/21 has a tapered outboard end 23 and a flared inboard end 24 whose purpose and function will be described presently.

Turning now to FIGS. 2 and 4, it can be seen that the intermediate flossing unit 12 comprises a length of flexible plastic yarn 30 whose opposite ends are affixed to the flared inboard ends 24 of each of the deformable end units 11 by chemical or thermal bonding or the like.

In addition, in the preferred embodiment of this invention, the deformable metal wire 20 is approximately 14 gauge in thickness and the end units have a generally uniform 2 mm diameter. Furthermore, the combined length from 70–75 mm and the intermediate unit 12 ranging in length from 90–100 mm.

As can best be appreciated by reference to FIGS. 5A through 5C, the floss construction 10 is employed to clean the support posts 101 of a dental implant 100 by first deforming the outboard end 23 of one of the end units 11 into a generally V-shaped configuration and inserting chosen outboard end 23 between a person's gum line and the dental implant 100 adjacent one of the support posts 101 as shown in FIG. 5A.

At this juncture, the other end unit 11 is grasped and withdrawn in a direction away from the user's mouth to captively surround the chosen support post 10; wherein, the bent end will project outwardly from beneath the implant 100 as depicted in FIG. 5B.

Then the user grasps the free end to position the length of plastic yarn 30 adjacent the support post 101 and the back and forth reciprocation of the end units 11 will cause the intermediate flossing unit 12 to scrub the periphery of the support post 101 in a well recognized manner to remove food and plaque particles therefrom.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

What is claimed is:

1. An improved dental floss construction for removing plaque and food particles from the periphery of metal support posts for dental implants wherein the dental floss construction comprises a pair of deformable end units wherein each end unit includes a very thin malleable strand of wire surrounded by a very thin layer of flexible plastic; and, an intermediate flossing unit operatively connected to one end of each end unit and including a length of flexible flossing material.

2. The construction as in claim 1; wherein, each of the malleable strands of wire has an inboard end and an outboard end wherein the length of flexible flossing material is suspended between the inboard ends of the malleable strands of wire.

3. The construction as in claim 2; wherein, the inboard ends of the strands of wire are flared.

4. The construction as in claim 3; wherein, the flexible flossing material comprises a length of plastic yarn.

5. The construction as in claim 2; wherein, the flexible flossing material comprises a length of plastic yarn.

6. The construction as in claim 1; wherein, the flexible flossing material comprises a length of plastic yarn.

7. The construction as in claim 1; wherein, the diameter of the deformable end unit is approximately 2 mm.

8. The construction as in claim 7; wherein, the combined length of the pair of deformable end units and the intermediate flossing unit are approximately 240 mm.

9. The construction as in claim 8; wherein, the length of each of the end units ranges from 70 to 75 mm and the length of the intermediate flossing unit ranges from 90 to 100 mm.

10. The construction as in claim 9; wherein, the length of each of the end units ranges from 70 to 75 mm and the length of the intermediate flossing unit ranges from 90 to 100 mm.

11. The construction as in claim 1; wherein, the combined length of the pair of deformable end units and the intermediate flossing unit are approximately 240 mm.

12. The construction as in claim 7; wherein, the malleable strands of wire are approximately 14 gauge in diameter.

* * * * *